United States Patent
Ulrich et al.

(10) Patent No.: US 7,385,210 B2
(45) Date of Patent: Jun. 10, 2008

(54) DEVICE FOR SPECTROSCOPY USING CHARGED ANALYTES

(75) Inventors: Andreas Ulrich, Dachau (DE); Wolfgang Baether, Luebeck (DE); Jochen Wieser, Munich (DE)

(73) Assignees: Technische Universitaet Muenchen (DE); Draegerwerk Aktiengesellschaft (DE); Coherent GmbH (DE)

( * ) Notice: Subject to any disclaimer, the term of this patent is extended or adjusted under 35 U.S.C. 154(b) by 171 days.

(21) Appl. No.: 11/471,426

(22) Filed: Jun. 20, 2006

(65) Prior Publication Data

US 2007/0023637 A1    Feb. 1, 2007

(30) Foreign Application Priority Data

Jun. 22, 2005  (DE) ............ 10 2005 028 930

(51) Int. Cl.
*H01J 49/00* (2006.01)
*H01J 49/08* (2006.01)
*B01D 59/44* (2006.01)

(52) U.S. Cl. .............. 250/492.3; 250/397; 204/403.06; 204/450; 204/452; 422/68.1; 435/183

(58) Field of Classification Search ............ None
See application file for complete search history.

(56) References Cited

U.S. PATENT DOCUMENTS

| | | | |
|---|---|---|---|
| 3,699,333 A | 10/1972 | Cohen et al. | 250/41.9 TF |
| 3,742,213 A | 6/1973 | Cohen et al. | 250/41.9 |
| 3,815,094 A | 6/1974 | Smith | 340/172.5 |
| 4,455,561 A | 6/1984 | Boyden et al. | 346/140 R |
| 4,839,143 A | 6/1989 | Vora et al. | 422/98 |
| 4,928,033 A | 5/1990 | Spangler et al. | 313/345 |
| 5,234,838 A | 8/1993 | Bacon, Jr. | 436/173 |
| 5,338,931 A | 8/1994 | Spangler et al. | 250/287 |
| 5,391,958 A | 2/1995 | Kelly | 313/420 |
| 5,414,267 A | 5/1995 | Wakalopulos | 250/492.3 |
| 5,684,300 A | 11/1997 | Taylor et al. | 250/286 |
| 5,968,837 A | 10/1999 | Döring et al. | 436/173 |
| 5,969,349 A | 10/1999 | Budovich et al. | 250/286 |
| 6,023,169 A | 2/2000 | Budovich et al. | 324/464 |
| 6,052,401 A * | 4/2000 | Wieser et al. | 372/74 |
| 6,264,825 B1 * | 7/2001 | Blackburn et al. | 205/777.5 |
| 6,282,222 B1 * | 8/2001 | Wieser et al. | 372/74 |
| 6,429,426 B1 | 8/2002 | Döring | 250/288 |

(Continued)

FOREIGN PATENT DOCUMENTS

DE    196 27 620    11/1997

(Continued)

OTHER PUBLICATIONS

Search Report from British Patent Office, Nov. 29, 2006, 1 page.

*Primary Examiner*—Nikita Wells
(74) *Attorney, Agent, or Firm*—St. Onge Steward Johnston & Reens LLC

(57) ABSTRACT

A device for spectroscopy using charged analytes has an electron generator, which sends electrons through membrane into a charging chamber. The thermal strain of the membrane may be lowered significantly if a material is selected for the membrane which contains at least one component from the group of oxides, nitrides, and carbides with at least one of the elements B, Al, C, Si, and Ti or polysilicon.

18 Claims, 4 Drawing Sheets

U.S. PATENT DOCUMENTS

| | | | |
|---|---|---|---|
| 7,087,148 B1 * | 8/2006 | Blackburn et al. | 205/452 |
| 2005/0117621 A1 | 6/2005 | Kraus | 372/74 |

FOREIGN PATENT DOCUMENTS

| | | |
|---|---|---|
| DE | 196 27 621 | 1/1998 |
| DE | 199 33 650 | 3/2001 |
| DE | 102 09 642 | 9/2003 |
| EP | 0 795 749 | 9/1997 |
| GB | 2 315 155 | 1/1998 |
| WO | WO 92/12529 | 7/1992 |
| WO | WO 2004/048964 | 6/2004 |
| WO | WO 2004/097882 | 11/2004 |
| WO | WO 2005/086742 | 9/2005 |

* cited by examiner

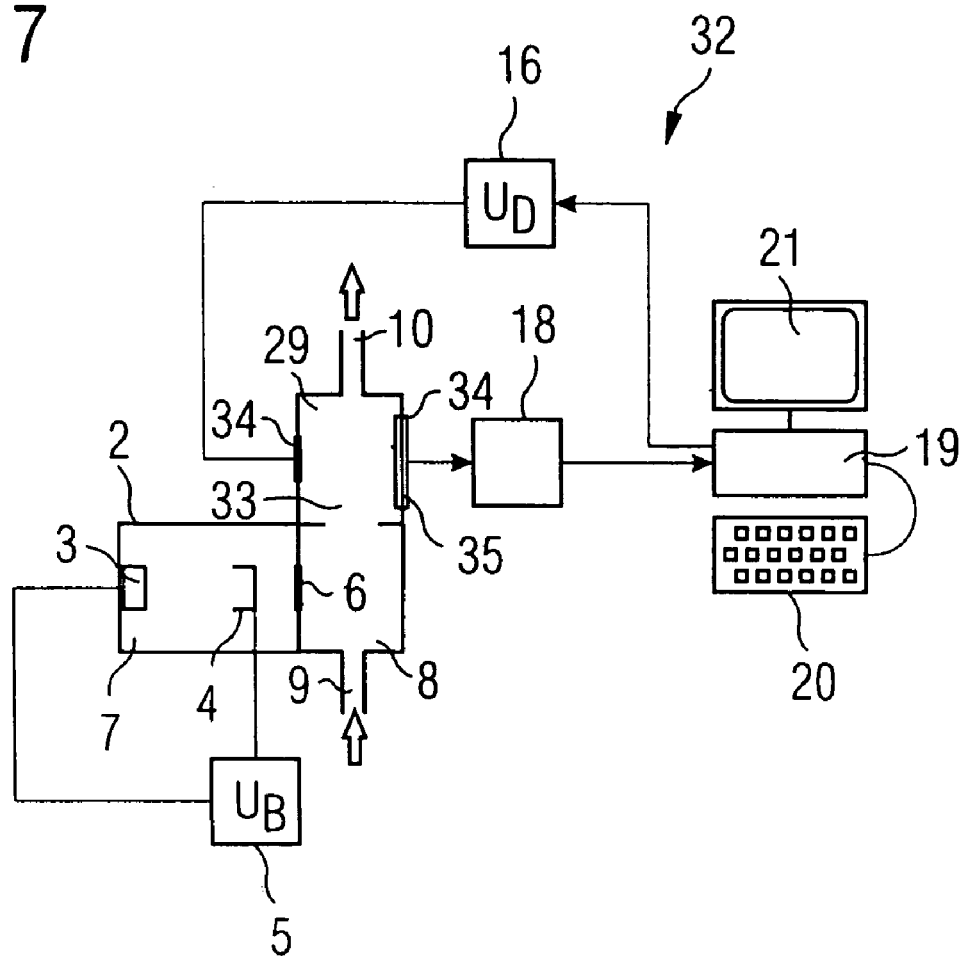

DEVICE FOR SPECTROSCOPY USING CHARGED ANALYTES

CROSS-REFERENCE TO RELATED APPLICATIONS

This application claims priority of German Application No. 10 2005 028 930.4 filed on Jun. 22, 2005.

FIELD OF THE INVENTION

The present invention relates to a device for spectroscopy using charged analytes having a gas chamber, which has a gas inlet and a charging chamber for forming charged analytes, a detector for detecting the charged analytes, a drift generator, which causes drift of charged analytes to the detector, and having an electron generator, which is separated from the gas chamber by a gas-tight membrane permeable to electrons and sends the electrons through the membrane into the charging chamber.

BACKGROUND OF THE INVENTION

A device of this type for ion mobility spectroscopy is known from DE 196 27 621 A1. The gas chamber is composed of a drift chamber and a partial chamber of a reaction chamber therein. A thermal electron emitter for generating free electrons is located in a further evacuated partial chamber of the reaction chamber. The free electrons are accelerated with the aid of an electron flux modulator and an acceleration voltage applied between the electron emitter and the electron flux modulator in the direction of an electron-permeable gas-tight membrane between the two partial chambers of the reaction chamber. The membrane is manufactured from mica and is coated on the side facing toward the gas-filled partial chamber of the reaction chamber with a metal layer.

The accelerated electrons enter the partial chamber of the reaction chamber, which is filled with drift gas and analyte gas, through the membrane. The charged gas particles arise in this partial chamber due to the incident electrons. The area of the gas chamber directly neighboring the membrane, in which the incident electrons are absorbed, is therefore to be identified in the following as the charging chamber.

The charging of the gas particles also results in formation of charged analytes. Under the effect of a drift voltage applied between the metallic coating of the membrane and the drift chamber, the charged analytes move from the gas-filled partial chamber of the reaction chamber to a capture electrode situated in the drift chamber and are detected there. Since the different charged analytes have different mobilities and thus different drift velocities, the different analytes require different amounts of time in order to reach the capture electrodes from the charging region placed in front of the membrane.

Ion mobility spectrometers are suitable in particular for detecting organic materials. For example, it is possible to detect organic compounds, such as chemical warfare agents, illegal drugs, or explosive materials in extremely small quantities with the aid of an ion mobility spectrometer.

An advantage of the known ion mobility spectrometer is that it manages without a radioactive source for charging the analytes. Therefore, no special protective measures have to be taken.

However, a disadvantage of the known ion mobility spectrometer is the high thermal strain of the membrane by the electron beam, because of which a support grating is situated on the entry side of the membrane, which mechanically stabilizes the membrane.

The known ion mobility spectrometer is thus not suitable for maintenance-free long-term use. Vice versa, however, there is a need for devices requiring as little maintenance as possible, in order to provide them to fire departments or units of the disaster protection office, for example.

Furthermore, an electron capture detector for gas chromatography, in which electrons generated with the aid of ultraviolet light are emitted through a membrane into a charging chamber, where electron-attracting molecules are charged and detected by collection electrodes, is known from DE 196 27 620 C1.

Moreover, a light source for ultraviolet light is known from U.S. Pat. No. 6,282,222 B1. The known light source uses excimers to generate the ultraviolet light, which are formed in a gas chamber through the effect of an electron beam on noble gas. The electron beam is generated by an electron generator which has an evacuated chamber having a thermal electron emitter. The electrons released by the electron emitter are accelerated in the direction of a metallic anode, which has a central hole which is covered by a carrier. The carrier holds a thin film. The film is preferably produced on the basis of silicon nitride, but may also be produced from a material of the group of carbides, nitrides, hydride, and oxides of metals, which are selected from the group of the elements B, Al, Si. Furthermore, polysilicon is suggested as a material for the membrane. The electron generator is separated from the gas chamber by the membrane.

SUMMARY OF THE INVENTION

Proceeding from this related art, the present invention is based on the object of providing a device for spectroscopy using charged analytes which is improved in regard to the stability.

This object is achieved by a device having the features of the independent claim. Advantageous embodiments and refinements are specified in claims dependent thereon.

In the device for spectroscopy using charged analytes, the membrane is produced from at least one material which contains at least one component from the group of oxides and nitrides with at least one of the elements B, Al, C, Si, and Ti as well as carbides with at least one of the elements B, Al, Si, and Ti or polysilicon.

Membranes made of these materials may be manufactured mechanically stably in a thickness which is significantly less than the half-thickness of the incident electrons, even if the kinetic energy of the incident electrons is below 50 keV. In this context, the half-thickness is to be understood as the thickness at which the power transmission is 50%.

The mechanical stability of membranes of this type is also sufficient to withstand the pressure difference between atmospheric pressure and vacuum. Since the thickness of the membrane is significantly less than the half-thicknesses in the energy range of interest, only a small part of the electrons are absorbed in the membrane. The thermal strain of the membrane is thus significantly less then in the related art. Because of the high strength and the low thermal strain, it is also not necessary to provide a support grating for the membrane. Furthermore, it may be assumed that the membrane remains stable over a long service life. A largely maintenance-free ion mobility spectrometer results, which may be used even by personnel who are not specially trained.

In a special embodiment, the membrane is implemented as multilayered, in particular having an oxide layer and a nitride layer. Using this multilayered design, the mechanical stability may be improved.

The thickness of the membrane is preferably in the range between 50 and 500 nm. A membrane in this thickness range has, for relevant diameters of a round opening to be covered in the range from one half to 2 mm, a sufficient mechanical strength to withstand the pressure differential between atmospheric pressure and vacuum. Rectangular openings whose narrow side is smaller than 2 mm may also be covered using a membrane of this type. Furthermore, the thickness of membranes of this type is significantly less than the half-thickness for electron energies less than 50 keV, so that a power transmission well above 50% is achievable.

The electron generator preferably comprises an electron source which emits electrons which are accelerated by an acceleration generator in the direction toward the membrane. Since the space requirement of an electron generator of this type is in the range of approximately 1 cm$^3$, an electron generator of this type may also be used for portable devices.

The kinetic energy of the electrons incident on the membrane is preferably to be in the range between 5 and 50 keV. In this energy range, the energy deposition depth in air is only a few millimeters. The charging area, in which the molecules are excited and charged, has correspondingly small dimensions. As a result, the charging chamber may also be kept small. The cited energy range for the kinetic energy of the electrons therefore particularly comes into consideration for portable devices having small constructions.

In a further preferred embodiment, the membrane is implemented without metallic electrodes. Since the attenuation of an electron beam is greater the greater the atomic number Z of the material, an electron beam in metals having especially high atomic number Z is attenuated especially strongly. For low energy absorption in the membrane, it is thus advantageous if the membrane is free of layers made of metals having a high atomic number Z if possible.

In order to ensure the transport of the charge carriers formed in the charging chamber to a drift chamber of the gas chamber in spite of a lack of metallic electrodes, the charging chamber adjoining the membrane is subjected to a gas flow, through which the charged components of the gas are transported to the drift chamber.

In a preferred embodiment, an intermediate chamber is located between the charging chamber and the drift chamber, in which a deflector electrode is implemented, with the aid of which the charged analytes collected in the intermediate chamber are transportable into the drift chamber. Therefore, in this case, metal coating of the membrane may be dispensed with, which results in improved transmission of the membrane.

The gas inlet for the analytes may be connected to the charging chamber. In this case, only charged analytes, whose lifetime is greater than the transport time for the path from the charging chamber into the intermediate chamber, reach the intermediate chamber. As a result, only especially stable charged analytes reach the drift chamber.

The gas inlet for the analytes may also be connected to the intermediate chamber while the charging chamber is flushed by a carrier gas free of analytes, however. In this case, the analytes do not come into contact with the heated surface of the membrane, so that the analytes remain unchanged.

In an especially compact construction, the charged analytes are transported into a drift chamber directly adjoining the charging chamber by a gas flow leading past the membrane. A deflection device implemented in the drift chamber generates a deflection force oriented transversely to the flow direction of the analyte gas, which deflects the charged analytes to a detector. Depending on mobility, the different types of charged analytes will cover different paths in the drift chamber and will be incident on different elements of the line detector.

Besides, the deflection force may also be varied if only one detector element is available.

BRIEF DESCRIPTION OF THE DRAWINGS

Further advantages and properties of the present invention are disclosed in the following description, in which exemplary embodiments of the present invention are explained in detail on the basis of the drawing.

FIG. 7 shows the construction of an especially compact form of an ion mobility spectrometer.

DETAILED DESCRIPTION OF THE INVENTION

Figure 1:
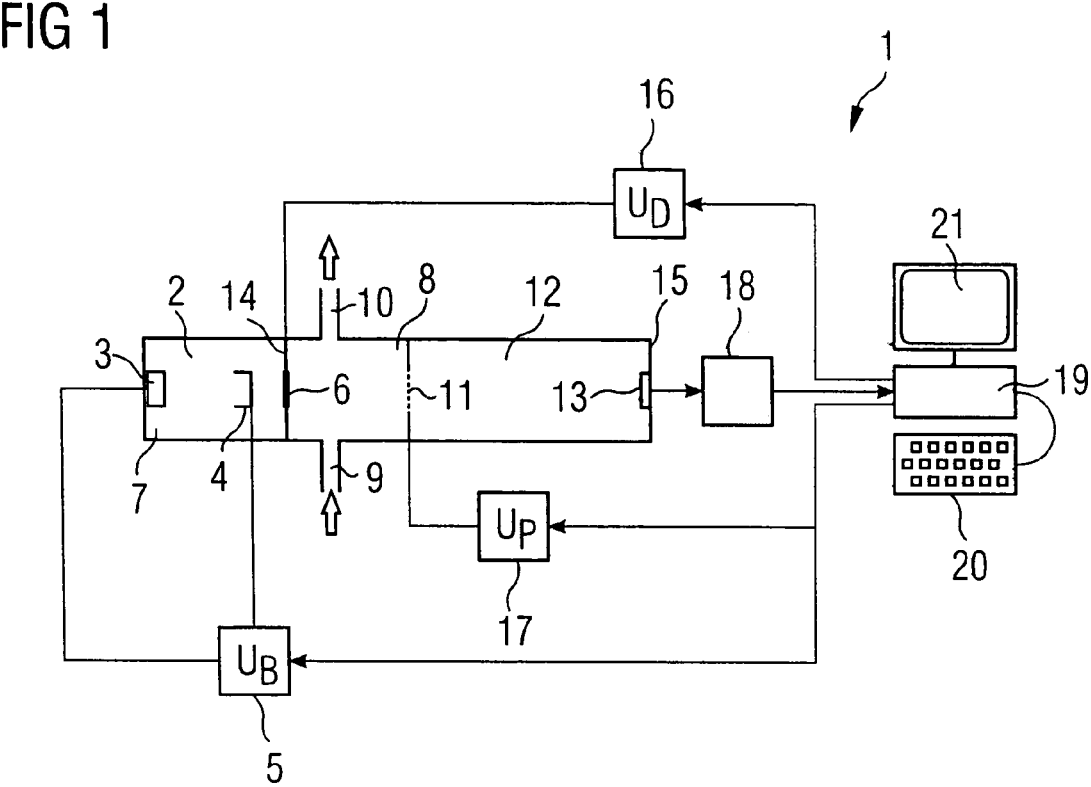
FIG. 1 shows the construction of an ion mobility spectrometer.

FIG. 1 shows an ion mobility spectrometer 1, which has an electron generator 2 for generating free electrons. This electron generator 2 comprises an electron emitter 3, which is a heating coil, for example, which emits electrons through thermionic emission. The electron generator 2 also has an acceleration anode 4. An acceleration voltage $U_B$, which is generated by an acceleration voltage source 5, is applied between the electron emitter 3 and the acceleration anode 4. A gas-tight electron-permeable membrane 6 is located in the beam direction behind the acceleration anode 4, which separates the generator chamber 7 from an ionization chamber 8, which has the function of the charging chamber in the ion mobility spectrometer 1 as in all other embodiments. A sample gas inlet 9 and a sample gas outlet 10 are connected to the ionization chamber 8.

A barrier grating 11 in turn separates the ionization chamber 8 from a drift chamber 12, which comprises multiple annular electrodes situated one behind another, which are not shown in FIG. 1. A detector 13 is located at the end of the drift chamber 12. In order to cause charged gas particles to drift from the membrane 6 to the detector 13, a deflector 14 in the form of a thin metal layer applied to the membrane 6 is implemented on the membrane 6. Furthermore, a drift voltage $U_d$, which is generated by a drift voltage source 16, is applied between the deflector 14 and a terminal electrode 15 of the drift chamber 12.

To control the drift from the membrane 6 to the detector 13, a pulse voltage $U_P$, which is provided by a pulse voltage source 17, may be applied to the barrier grating 11. Finally, the detector 13 is connected to a signal processing unit 18, which applies data to a control unit 19. The control unit 19 may be a commercially available computer having keyboard 20 and monitor 21. The control unit 19 and the devices required for providing a graphic user interface may form a unit with the actual ion mobility spectrometer 1, however. In particular, the monitor 21 may also be replaced by a single warning light which indicates the detection of a specific substance.

During operation of the ion mobility spectrometer 1, electrons are emitted from the electron generator 2 through the membrane 6 into the ionization chamber 8. In the ionization chamber 8, the accelerated electrons ionize the gas molecules. Essentially, diverse hydronium ions $H_+(H_2O)_n$ first arise. In the spectrum of the ion mobility spectrometer 1, these hydronium ions form the reactant ion peak (=RIP). The hydronium ions now react with analyte molecules with proton transfer. Protonated analyte molecules arise, inter alia, which are also referred to in the following as analyte ions. Through a voltage pulse at the barrier grating 11, the analyte ions are conveyed in packets into the drift chamber 12, where the analyte ions drift at different speeds, depending on mobility, through the drift gas to the detector 13 under the influence of the drift voltage $U_d$. The analyte ions typically have different mobilities than the reactant ions and may thus be separated from the reactant ions in the drift chamber 12. The time which the analyte ions or reactant ions require to pass through the drift chamber 12 is thus characteristic of the particular type of ions. The concentration of different analytes in the sample gas may thus be concluded from the curve of the detector current.

Figure 2:
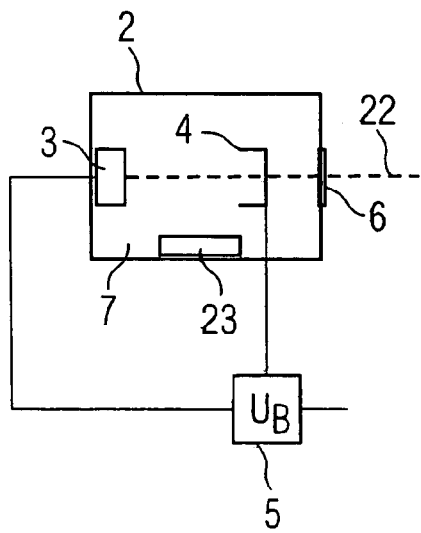
FIG. 2 shows the construction of an electron generator.

The electron generator 2 will now be explained in greater detail in the following on the basis of FIG. 2. The electron emitter 3 may be a device for thermionic emission, photo-emission, or field emission. The latter is preferred because of the low power consumption. The electrons emitted by the electron emitter 3 are accelerated by the acceleration anode 4 in the direction of the membrane 6. An electron beam 22 arises which passes through the membrane 6. The vacuum in the generator chamber 7 is produced using a vacuum pump, but is preferably maintained using a getter 23 situated in the generator chamber 7 at an overall size required for a portable device. The essential advantage of the electron generator 2 is that it may be turned on and off nearly arbitrarily. This allows operation using nearly arbitrary time structures. Thus, the electron generator may be operated both using short pulses and also continuously.

Figure 3:
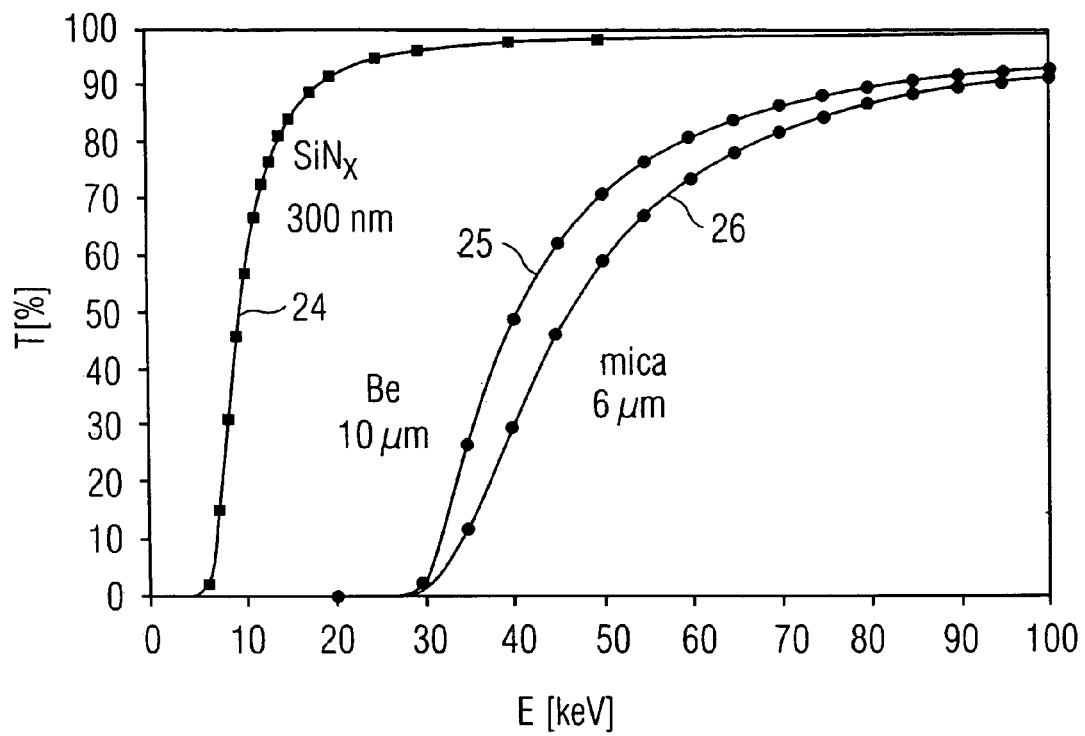
FIG. 3 shows a diagram in which the power transmission of membranes made of different materials is plotted against the energy of the incident electrons.

FIG. 3 shows a diagram in which the power transmission T is plotted as a function of the energy E of the incident electrons for membranes made of different materials. A transmission curve 24 represents the power transmission of a membrane made of silicon nitride at a thickness of 300 nm. Besides great mechanical strength, silicon nitride also offers the advantage that it is commonly produced in the field of the semiconductor industry.

Further transmission curves 25 and 26 identify the power transmission of a 10 μm thick membrane based on beryllium and a 6 μm thick membrane manufactured from mica. The transmission curves 24 through 26 were each calculated with the aid of the program CASINO by Drouin, Couture, Gauvin, Hovington, Horny, and Demers. It is noticeable that the 300 nm thick membrane based on SiNx already transmits electrons having energies from approximately 5 keV. In addition, the slope of the power transmission is very steep. If the electrons have a kinetic energy of approximately 10 keV, a power transmission of approximately 50% is obtained, and the power transmission reaches a value in the range of 85% at a kinetic energy of 15 keV. Therefore, the thermal strain of the membrane 6 is significantly lower in the energy range cited than with membranes made of beryllium and mica. The cause of this is the significantly lower thickness of the membrane 6 based on silicon nitride.

Figure 4:
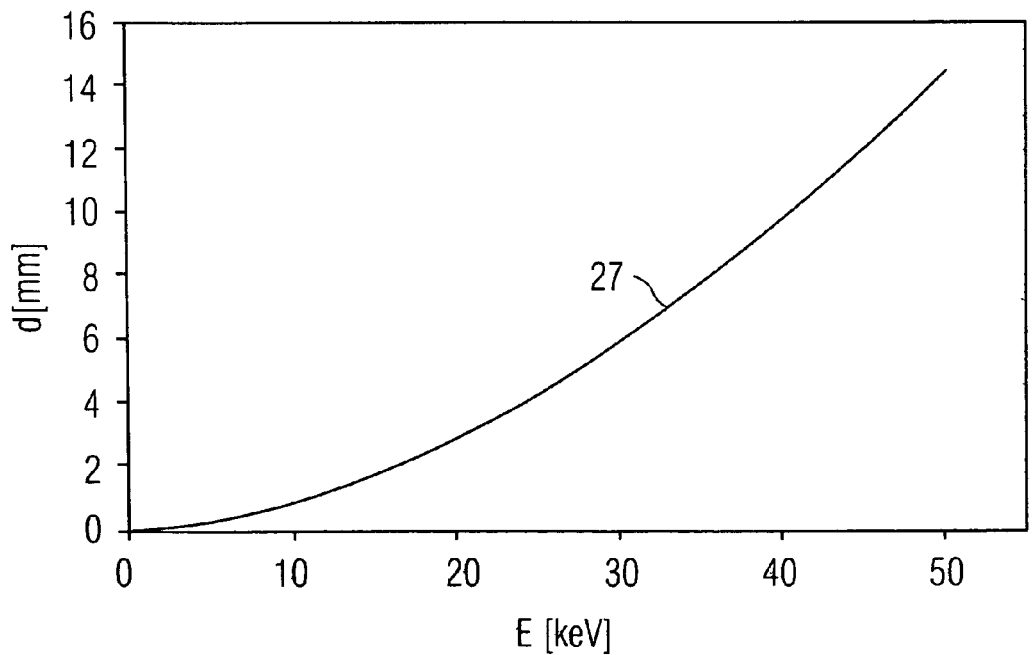
FIG. 4 shows a diagram in which the energy deposition depth in nitrogen at atmospheric pressure is plotted against the energy of the incident electrons.

It is also possible according to the transmission curves 25 and 26 to reach a power transmission in the range of 90% with electron energies in the range of 100 keV using membranes based on beryllium or mica. However, electrons having an energy in the range of 100 keV have a range of approximately 30 cm in air. In contrast, electrons having an energy below 50 keV only have a range of less than 15 mm according to a depth curve 27 shown in FIG. 4. The depth curve 27 in FIG. 4 shows the energy deposition depth d in nitrogen at atmospheric pressure as a function of the electron energy E according to S. Valkealahti, et al., J. Appl. Phys. 65, 2258 (1989). The relationship shown in FIG. 4 makes it clear that in the event of a restriction of the electron energies to values below 50 keV, a compact construction of the ionization chamber 8 is possible.

It is to be noted that materials based on nitrides and oxides with at least one of the elements B, Al, C, Si, and Ti as well as carbides with at least one of the elements Al, C, Si, and Ti also come into consideration for the membranes. Membranes made of polysilicon may also be manufactured sufficiently thin.

The thickness of the membrane 6 is to be selected as between 50 and 500 nm, preferably in the range from 200 to 300 nm.

In this thickness range of the membrane 6, the electron generator 2 is to accelerate the electrons to energies in the range from 5 to 50 keV, particularly to energies in the range from 5 to 20 keV, preferably to energies below 15 keV.

The electron generator 2 generates currents in the range from 1 picoampere to 10 microamperes, preferably currents of approximately 100 nanoamperes.

In addition, the electron generator 2 may be operated both continuously and also pulsed using pulse durations in the range from 5 ns. Typical pulse durations are the range from 1 ms to 20 ms.

Figure 5:
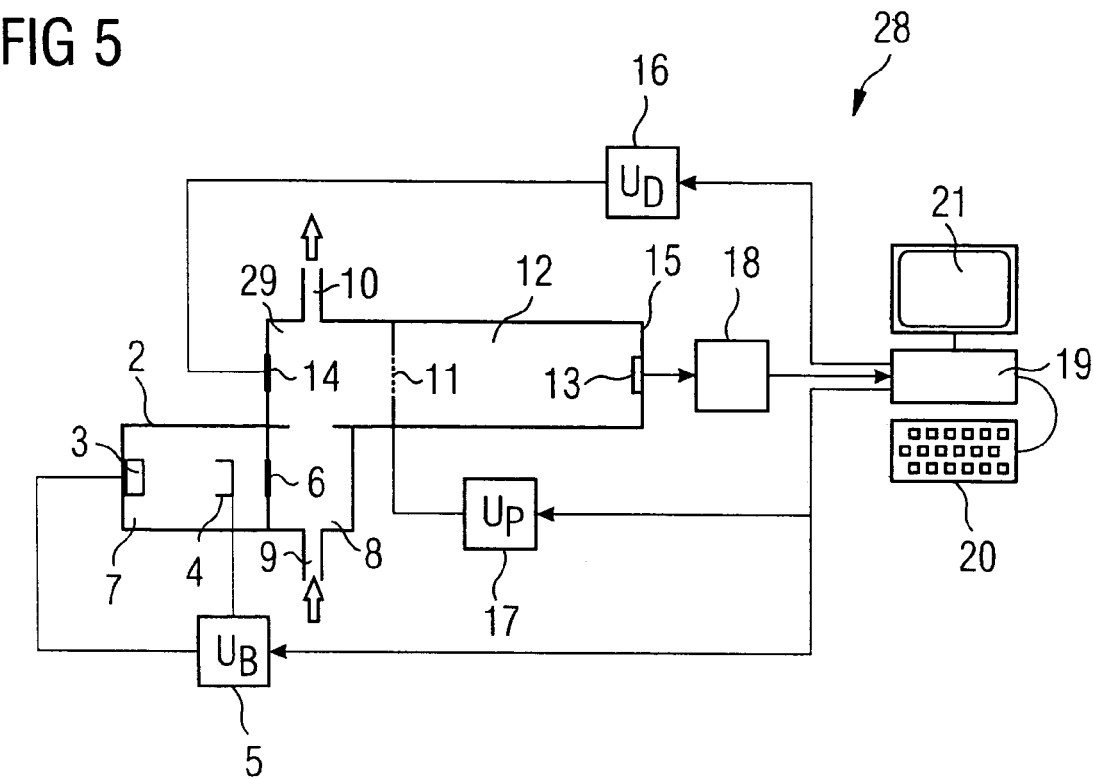
FIG. 5 shows the construction of a further ion mobility spectrometer, in which the drift chamber is separated from the ionization chamber by an intermediate chamber.

A further ion mobility spectrometer 28 is shown in FIG. 5, in which a deflector chamber 29 is situated between the ionization chamber 8 and the drift chamber 12. The deflector 14 is also located in the deflector chamber 29, to which the drift voltage $U_d$ is applied. The sample gas inlet 9 is implemented on the ionization chamber 8, while the sample gas outlet 10 is attached to the deflector chamber 29. Therefore, a gas flow occurs both in the ionization chamber 8 and also in the deflector chamber 29, which transports excimers or ionized molecules generated in front of the membrane 6 in the ionization chamber 8 by the electron beam 22 into the deflector chamber 29, where they may be conveyed by a suitable voltage pulse output by the pulse voltage source 17 into the drift chamber 12.

The special feature of the ion mobility spectrometer 28 is that the membrane 6 does not have to be provided with a metallic layer made of a metal having a high atomic number Z, which additionally attenuates the electron beam 22. Rather, the transport from the ionization chamber to the deflector 14 is performed by the gas flow, which flows through the ionization chamber 8 and the deflector chamber 29. The membrane 6 may in principle also be provided with a thin aluminum layer, but such a layer is frequently chemically unstable, because of which it is advantageous if such a layer may be dispensed with.

The spatial separation of ionization chamber 8 and deflector chamber 29 is also advisable to allow highly reactive ions to react during the transport from the ionization chamber 8 into the deflection chamber 29. This is because only those ions which live longer than the required transport time reach the deflector chamber 29. Thus, only stable analyte ions reach the drift chamber 12 in the ion mobility spectrometer 28.

Through the selection of the time structure for the electron beam 22, the flow velocity of the gas, and the time structure of the pulse voltage $U_P$, as well as the size of the drift voltage $U_D$, specific types of charged analyte may be generated and detected in a targeted way.

Figure 6:
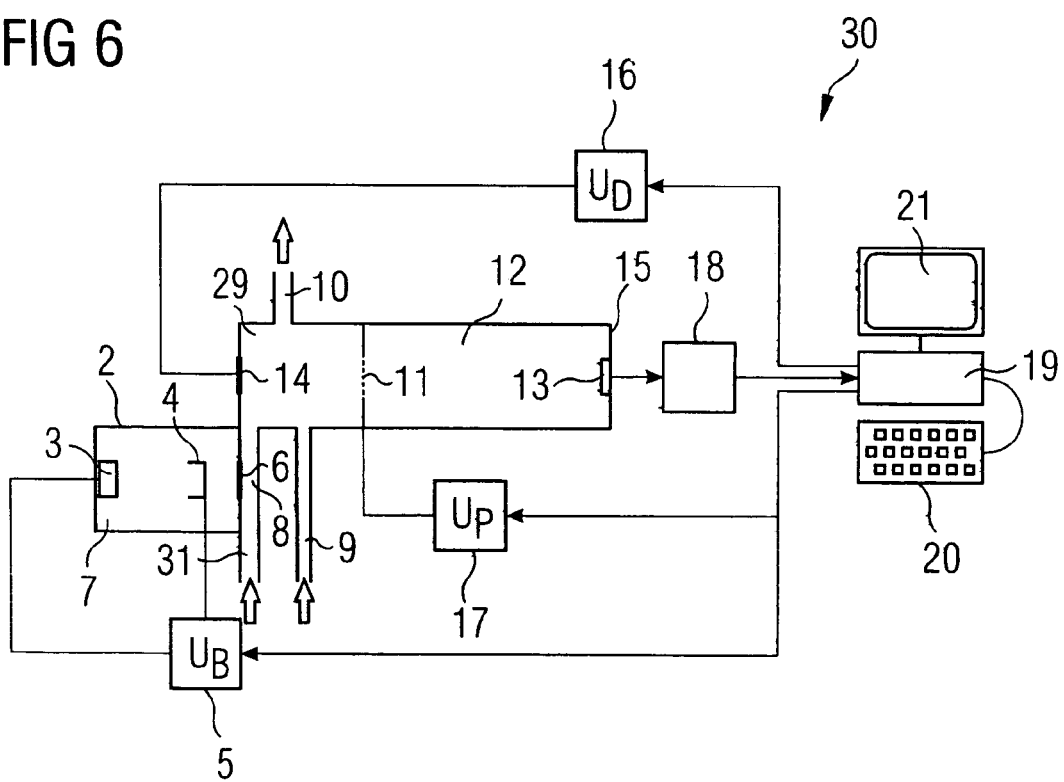
FIG. 6 shows the construction of an ion mobility spectrometer, in which the analyte inlet is connected to the intermediate chamber.

Finally, a further ion mobility spectrometer 30 is shown in FIG. 6, in which the ionization chamber 8 is implemented as a gas line, through which carrier gas is conducted past the membrane 6 from a carrier gas connection 31. The sample gas inlet 9, in contrast, is located at the ionization chamber 8. In the ion mobility spectrometer 30, the analyte molecules are thus guided past the possibly strongly heated membrane 6. Thus, only the diverse hydronium ions are generated in the ionization chamber 8, which is implemented as a gas line for the carrier gas. These are transported using the carrier gas flow into the deflector chamber 29 and then react selectively with the analyte molecules supplied there to form the desired analyte ions.

Finally, the ion mobility spectrometer 32 shown in FIG. 7 has an especially compact construction. In the ion mobility spectrometer 32, the sample gas inlet 9 is attached at the ionization chamber 8. A drift chamber 33, at which the sample gas outlet 10 is also connected, is placed directly at the ionization chamber 8. Therefore, a gas flow occurs through the ionization chamber 8 and the drift chamber 33 which conveys the analyte ions from the ionization chamber 8 into the drift chamber 33.

The drift chamber 33 comprises deflection electrodes 34 on diametrically opposing sides, which generate a deflection force oriented transversely to the gas flow in the drift chamber 33, which deflects the analyte ions to a detector line 35. Analyte ions of higher mobility are more strongly deflected than analyte ions of lesser mobility in this case. The analyte ions of higher mobility are thus incident on different elements of the detector line 35 than the analyte ions of lesser mobility. If only a single analyte ion detector is provided, the deflection voltage may also be varied between the deflection electrodes 34 if necessary.

The ion mobility spectrometers 1, 28, 30, and 32 described here each have an especially small construction. They are therefore suitable for portable embodiments. Furthermore, a high degree of stability may be expected from the ion mobility spectrometers 1, 28, 30, and 32. The ion mobility spectrometers 1, 28, 30, and 32 may thus be operated even by personnel who are not specially trained.

It is to be noted that the membranes described here may also be used in connection with an electron capture detector or other spectrometers operating using charged analytes.

What is claimed is:

1. A device for spectroscopy using charged analytes comprising:
    a gas chamber, which has a gas inlet and a charging chamber for forming charged analytes,
    a detector for detecting the charged analytes,
    a drift generator, which causes a drift of charged analytes to the detector,
    an electron generator, which is separated from the gas chamber by a gas-tight membrane, which is permeable to electrons, and sends the electrons through the membrane into the charging chamber,
    the membrane being produced from a material which contains polysilicon or at least one component from the group of oxides and nitrides with at least one of the elements B, Al, C, Si, and Ti as well as carbides with at least one of the elements B, Al, Si, and Ti.

2. The device according to claim 1, wherein the membrane is implemented as multilayered.

3. The device according to claim 2, wherein one layer of the membrane contains oxides and a further layer contains nitrides.

4. The device according to claim 1, wherein the membrane has a thickness below 500 nm.

5. The device according to claim 1, wherein the electron generator comprises an electron emitter and an acceleration generator for accelerating the electrons emitted by the electron emitter in the direction toward the membrane.

6. The device according to claim 5, wherein the acceleration generator accelerates the electrons to energies in the range between 5 and 50 keV.

7. The device according to claim 1, wherein charge carriers formed in the charging chamber are transportable from the charging chamber by a gas flow in the direction toward the detector.

8. The device according to claim 7, wherein the gas flow runs from a gas inlet, which is implemented on the charging chamber, to a gas outlet situated at a distance from the charging chamber.

9. The device according to claim 7, wherein the gas chamber comprises a drift chamber, which is divided by a barrier device and is provided with a detector.

10. The device according to claim 9, wherein an intermediate chamber, which is provided with a gas outlet, is implemented between drift chamber and charging chamber, which is provided with a conveyor unit, using which charged analytes are transportable from the intermediate chamber into the drift chamber.

11. The device according to claim 10, wherein analytes are conductible into the charging chamber through the gas inlet implemented on the charging chamber.

12. The device according to claim 10, wherein an analyte-free carrier gas may be fed into the gas inlet implemented on the charging chamber, and the intermediate chamber is provided with a gas inlet, using which analytes are conductible into the intermediate chamber.

13. The device according to claim 7, wherein a drift chamber, which is provided with a gas outlet, adjoins the charging chamber, in which charged analytes may be deflected transversely to the gas flow to a detector by a deflection device.

14. The device according to claim 13, wherein the charged analytes may be deflected to a detector line.

15. The device according to claim 13, wherein the deflection force acting on the charged analytes is variable.

16. The device according to claim 1, wherein the electron generator may be operated pulse using pulses greater than 5 ns up to continuously.

17. The device according to claim 8, wherein the gas chamber comprises a drift chamber, which is divided by a barrier device and is provided with a detector.

18. The device according to claim 8, wherein a drift chamber, which is provided with a gas outlet, adjoins the charging chamber, in which charged analytes may be deflected transversely to the gas flow to a detector by a deflection device.

* * * * *